(12) United States Patent
Nakamura

(10) Patent No.: US 9,588,175 B2
(45) Date of Patent: Mar. 7, 2017

(54) SEMICONDUCTOR DEVICE INSPECTION DEVICE AND SEMICONDUCTOR DEVICE INSPECTION METHOD

(71) Applicant: HAMAMATSU PHOTONICS K.K., Hamamatsu-shi, Shizuoka (JP)

(72) Inventor: Tomonori Nakamura, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 91 days.

(21) Appl. No.: 14/440,175

(22) PCT Filed: Oct. 25, 2013

(86) PCT No.: PCT/JP2013/078987
§ 371 (c)(1),
(2) Date: May 1, 2015

(87) PCT Pub. No.: WO2014/073398
PCT Pub. Date: May 15, 2014

(65) Prior Publication Data
US 2015/0276865 A1    Oct. 1, 2015

(30) Foreign Application Priority Data
Nov. 6, 2012  (JP) ................. 2012-244636

(51) Int. Cl.
*G01R 31/308*  (2006.01)
*G01R 31/311*  (2006.01)
(Continued)

(52) U.S. Cl.
CPC ..... *G01R 31/311* (2013.01); *G01N 21/95607* (2013.01); *G01R 1/071* (2013.01); *G01R 31/26* (2013.01); *G01R 31/2601* (2013.01); *G01R 31/2851* (2013.01); *G01R 31/308* (2013.01)

(58) Field of Classification Search
CPC .... G01R 1/071; G01R 31/26; G01R 31/2601; G01R 31/2851; G01R 31/308; G01R 31/311
USPC ......... 324/71, 378, 403, 415, 425, 500, 537, 324/754.01, 754.21, 754.23
See application file for complete search history.

(56) References Cited

U.S. PATENT DOCUMENTS

| | | | |
|---|---|---|---|
| 7,659,981 B2 | 2/2010 | Lo et al. | |
| 2007/0208222 A1* | 9/2007 | Miyoshi | A61B 5/06 600/117 |

(Continued)

FOREIGN PATENT DOCUMENTS

| | | |
|---|---|---|
| CN | 1879337 | 12/2006 |
| CN | 101501516 | 8/2009 |

(Continued)

*Primary Examiner* — Jermele M Hollington
*Assistant Examiner* — Raul Rios Russo
(74) *Attorney, Agent, or Firm* — Drinker Biddle & Reath LLP

(57) ABSTRACT

A semiconductor device inspection system (1) includes a laser beam source (2), for emitting light, an optical sensor (12) for detecting the light reflected by the semiconductor device (10) from the light and outputting a detection signal, a frequency band setting unit (16) for setting a measurement frequency band and a reference frequency band with respect to the detection signal, a spectrum analyzer (15) for generating a measurement signal and a reference signal from the detection signals in the measurement frequency band and the reference frequency band, and a signal acquisition unit (17) for calculating a difference between the measurement signal and the reference signal to acquire an analysis signal. The frequency band setting unit (16) sets the reference frequency band to a frequency domain in which a level of the detection signal is lower than a level obtained by adding 3 decibels to a white noise level serving as a reference.

12 Claims, 9 Drawing Sheets

(51) Int. Cl.
*G01R 31/28* (2006.01)
*G01R 31/26* (2014.01)
*G01R 1/07* (2006.01)
*G01N 21/956* (2006.01)
*G01R 31/302* (2006.01)

(56) References Cited

U.S. PATENT DOCUMENTS

2012/0019815 A1* 1/2012 Horikoshi .......... G01B 11/0691
356/217
2012/0025098 A1* 2/2012 Nakada ................ G01N 15/147
250/459.1

FOREIGN PATENT DOCUMENTS

| | | |
|---|---|---|
| JP | S63-218869 | 9/1988 |
| JP | H01-169862 A | 7/1989 |
| JP | H07-260891 A | 10/1995 |
| JP | H8-101232 | 4/1996 |
| JP | H10-084250 | 3/1998 |
| JP | H11-133118 | 5/1999 |
| JP | 2001-255354 A | 9/2001 |
| JP | 2004-144685 | 5/2004 |
| JP | 2005-109238 | 4/2005 |
| JP | 2007-064975 A | 3/2007 |
| JP | 2010-271307 A | 12/2010 |
| WO | WO-2006/011423 A1 | 2/2006 |
| WO | WO 2008/143101 | 11/2008 |

* cited by examiner

Fig.5
(a)
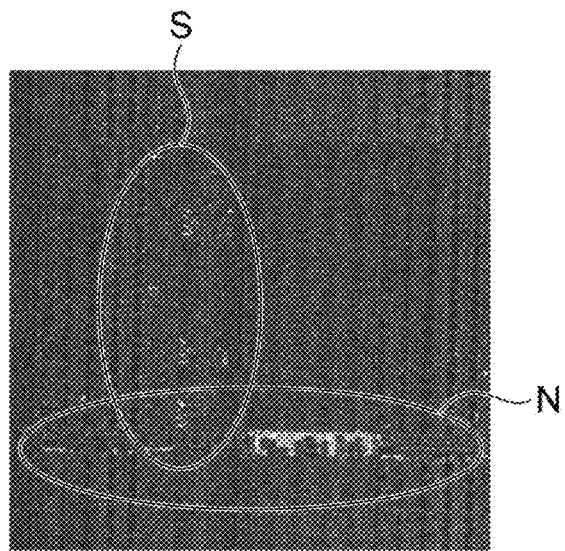
(b)
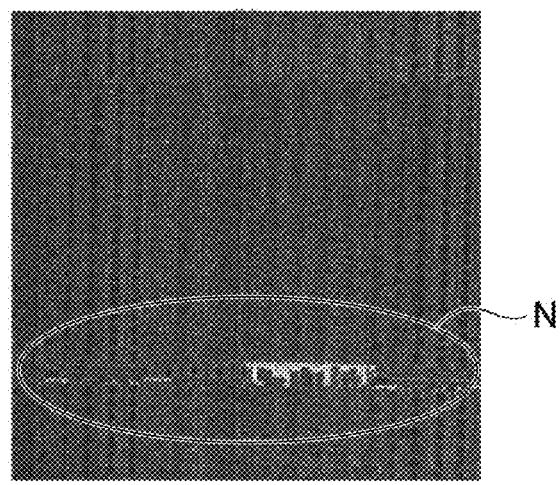
(c)
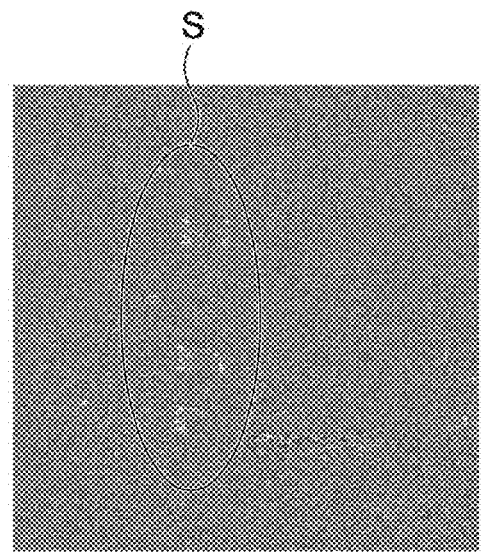

SEMICONDUCTOR DEVICE INSPECTION DEVICE AND SEMICONDUCTOR DEVICE INSPECTION METHOD

TECHNICAL FIELD

The present invention relates to a semiconductor device inspection system and a semiconductor device inspection method.

BACKGROUND ART

As a technology of inspecting an integrated circuit, an optical probing technology referred to as electro optical probing (EOP) or electro-optical frequency mapping (EOFM) is known. In the optical probing technology, light emitted from a light source is irradiated an integrated circuit, and the light reflected by the integrated circuit is detected by an optical sensor to acquire a detection signal. Then, in the acquired detection signal, a desired frequency is selected, and amplitude energy thereof is displayed as time progression or two-dimensional mapping is displayed. Accordingly, a position of the circuit operated at a desired frequency can be specified.

CITATION LIST

Patent Literature

[Patent Literature 1] Japanese Unexamined Patent Application, First Publication No. 2007-64975
[Patent Literature 2] Japanese Unexamined Patent Application, First Publication No. 2001-255354
[Patent Literature 3] Japanese Unexamined Patent Application, First Publication No. 2010-271307

SUMMARY OF INVENTION

Technical Problem

In the above-mentioned optical probing technology, since a modulation signal included in the reflected light is extremely small, S/N is defined by shot noise of the reflected light, excess noise of the light source, thermal noise of the optical sensor, and so on. For this reason, in order to secure sufficient S/N, it is necessary to extend a scan time or increase a quantity of light while using a stable light source.

However, the shot noise cannot be fundamentally removed, and a shot noise component cannot be prevented from overlapping a measurement result as a pattern image. Moreover, in addition to the shot noise component in proportion to a square root of the quantity of light, an excess noise component in proportion to the quantity of light also overlaps the measurement result. Accordingly, it is difficult to remove the shot noise and the excess noise in image processing of a simple pattern image.

Accordingly, the present invention is directed to provide a semiconductor device inspection system and a semiconductor device inspection method that are capable of reducing a measurement time and attempting high precision of a measurement result.

Solution to Problem

A semiconductor device inspection system according to an aspect of the present invention includes a light generating unit for generating light to be irradiated a semiconductor device serving as a device under test; a light detecting unit for detecting the light reflected by the semiconductor device when the light generated from the light generating unit is irradiated the semiconductor device and outputting a detection signal; a frequency band setting unit for setting a measurement frequency band and a reference frequency band with respect to the detection signal; a signal generating unit for generating a measurement signal from the detection signal in the measurement frequency band and for generating a reference signal from the detection signal in the reference frequency band; and a signal acquisition unit for by calculating a difference between the measurement signal and the reference signal to acquire an analysis signal, wherein, when a level of the detection signal is calculated based on power, the frequency band setting unit sets the reference frequency band to a frequency domain in which the level is lower than a level obtained by adding 3 decibels to a white noise level serving as a reference.

In the semiconductor device inspection system, the measurement signal and the reference signal are generated based on the detection signal in the measurement frequency band and the detection signal in the reference frequency band detected at the same timing. Here, when the level of the detection signal is calculated based on the power, the reference frequency band is set to the frequency domain in which the level is lower than the level obtained by adding 3 decibels to the white noise level serving as the reference. Accordingly, the analysis signal acquired by calculating the difference between the measurement signal and the reference signal is a signal from which shot noise, excess noise, and so on, are removed. In this way, since the detection signal in the measurement frequency band and the detection signal in the reference frequency band are detected at the same timing, in comparison with the case in which these are detected at separate timings, the measurement time can be reduced. Moreover, since the detection signal in the measurement frequency band and the detection signal in the reference frequency band are detected under the same condition, in comparison with the case in which these are detected under separate conditions, high precision of the measurement result can be attempted.

In the semiconductor device inspection system according to the aspect of the present invention, the frequency band setting unit may set the reference frequency band to the frequency domain having a frequency higher than the measurement frequency band. According to the configuration, an influence of the 1/F noise having a tendency to appear in a relatively low frequency domain can be suppressed from being applied to the detection signal in the measurement frequency band.

In the semiconductor device inspection system according to the aspect of the present invention, the frequency band setting unit may set the reference frequency band to include a frequency of a system noise included in the measurement frequency band. According to the configuration, as the difference between the measurement signal and the reference signal is calculated, the system noise can be removed from the analysis signal.

The semiconductor device inspection system according to the aspect of the present invention may further include an electrical signal application unit for applying a first electrical signal having a first modulation frequency to the semiconductor device, wherein the frequency band setting unit sets the measurement frequency band to include a frequency that is a natural number times the first modulation frequency. According to the configuration, setting of the measurement frequency band can be optimally performed.

In the semiconductor device inspection system according to the aspect of the present invention, the electrical signal application unit may apply a second electrical signal having a second modulation frequency different from the first modulation frequency to the semiconductor device together with the first electrical signal, and the frequency band setting unit may set the measurement frequency band to include a frequency that is a natural number times the first modulation frequency, and set the reference frequency band to include a frequency that is a natural number times the second modulation frequency. According to the configuration, in addition to the measurement frequency band, even in the reference frequency band, a separate analysis signal from which the shot noise, the excess noise, and so on, are removed can be acquired.

The semiconductor device inspection system according to the aspect of the present invention may further include a first power source for operating the light generating unit; and a second power source separately installed from the first power source and for operating the light detecting unit. In order to acquire the analysis signal from which the shot noise, the excess noise, and so on, are removed as the difference between the measurement signal and the reference signal is calculated, suppression of generation of the system noise in the frequency domain in which the reference frequency band is set is needed. Here, as the first power source and the second power source are separately installed, since there is no need to install a DD converter or the like that causes generation of the system noise, generation of the system noise in the frequency domain in which the reference frequency band is set can be suppressed.

In the semiconductor device inspection system according to the aspect of the present invention, the signal generating unit may include a spectrum analyzer for generating the measurement signal from the detection signal in the measurement frequency band and generating the reference signal from the detection signal in the reference frequency band. Alternatively, the signal generating unit may include a first lock-in amplifier for generating the measurement signal from the detection signal in the measurement frequency band, and a second lock-in amplifier for generating the reference signal from the detection signal in the reference frequency band. Alternatively, the signal generating unit may include a first spectrum analyzer for generating the measurement signal from the detection signal in the measurement frequency band, and a second spectrum analyzer for generating the reference signal from the detection signal in the reference frequency band. According to these configurations, the measurement signal and the reference signal can be efficiently generated based on the detection signal in the measurement frequency band and the detection signal in the reference frequency band detected at the same timing.

A semiconductor device inspection system according to an aspect of the present invention includes a light generating unit for generating light to be irradiated a semiconductor device serving as a device under test; a light detecting unit for detecting the light reflected by the semiconductor device and outputting a detection signal when the light generated from the light generating unit is irradiated the semiconductor device; a frequency band setting unit for setting a measurement frequency band and a reference frequency band with respect to the detection signal; a signal generating unit for generating a measurement signal from the detection signal in the measurement frequency band and generating a reference signal from the detection signal in the reference frequency band; and a signal acquisition unit for calculating a difference between the measurement signal and the reference signal to acquire an analysis signal, wherein, when a level of the detection signal is calculated based on amplitude energy, the frequency band setting unit sets the reference frequency band to a frequency domain in which the level is lower than a level obtained by adding 6 decibels to a white noise level serving as a reference.

A semiconductor device inspection method according to an aspect of the present invention includes a light detection step of irradiating a semiconductor device serving as a device under test with light, detecting the light reflected by the semiconductor device and outputting a detection signal; a frequency band setting step of setting a measurement frequency band and a reference frequency band with respect to the detection signal; a signal generating step of generating a measurement signal from the detection signal in the measurement frequency band and generating a reference signal from the detection signal in the reference frequency band; and a signal acquisition step of calculating a difference between the measurement signal and the reference signal to acquire an analysis signal, wherein, in the frequency band setting step, when a level of the detection signal is calculated based on power, the reference frequency band is set to a frequency domain in which the level is lower than a level obtained by adding 3 decibels to a white noise level serving as a reference.

A semiconductor device inspection method according to an aspect of the present invention includes a light detection step of irradiating a semiconductor device serving as a device under test with light, detecting the light reflected by the semiconductor device and outputting a detection signal; a frequency band setting step of setting a measurement frequency band and a reference frequency band with respect to the detection signal; a signal generating step of generating a measurement signal from the detection signal in the measurement frequency band and generating a reference signal from the detection signal in the reference frequency band; and a signal acquisition step of calculating a difference between the measurement signal and the reference signal to acquire an analysis signal, wherein, in the frequency band setting step, when a level of the detection signal is calculated based on amplitude energy, the reference frequency band is set to a frequency domain in which the level is lower than a level obtained by adding 6 decibels to a white noise level serving as a reference.

With the semiconductor device inspection system and the semiconductor device inspection method, reduction in measurement time and high precision of a measurement result can be achieved for the same reasons as in the above-mentioned semiconductor device inspection system.

Advantageous Effects of Invention

According to an aspect of the present invention, it is possible to provide the semiconductor device inspection system and the semiconductor device inspection method that are capable of reducing a measurement time and achieving high precision of a measurement result.

BRIEF DESCRIPTION OF DRAWINGS

FIG. 5 shows semiconductor device images based on a measurement signal, a reference signal and an analysis signal acquired by the semiconductor device inspection system of FIG. 1;

DESCRIPTION OF EMBODIMENTS

Figure 1:
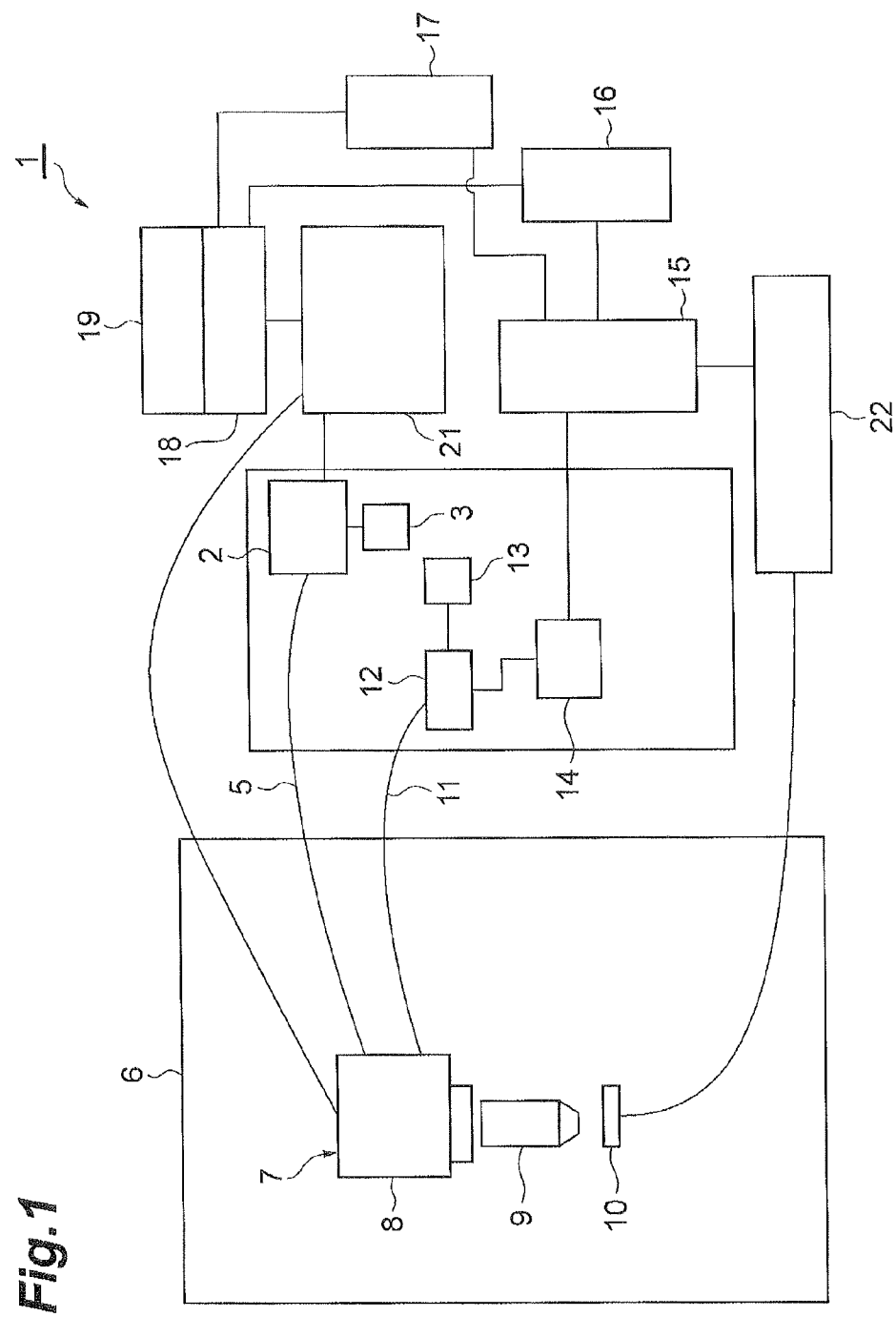
FIG. 1 is a configuration view of a semiconductor device inspection system of an embodiment of the present invention.

Hereinafter, embodiments of the present invention will be described in detail with reference to the accompanying drawings. Further, the same or corresponding portions of the drawings are designated by the same reference numerals, and overlapping description thereof will be omitted.

As shown in FIG. 1, a semiconductor device inspection system 1 is a device for inspecting a semiconductor device 10, for example, specifying a place in which an abnormality occurs in the semiconductor device 10 serving as a device under test (DUT), and so on. As the semiconductor device 10, there are provided an integrated circuit having a PN junction such as a transistor or the like (for example, a small scale integrated (SSI) circuit, a medium scale integrated (MSI) circuit, a large scale integrated (LSI) circuit, a very large scale integrated (VLSI) circuit, an ultra large scale integrated (ULSI) circuit, and a giga scale integrated (GSI) circuit), a MOS transistor for large current/high pressure, a bipolar transistor, and so on. In addition, the semiconductor device 10 may be a semiconductor device in which modulation is applied to a substrate by heat.

The semiconductor device inspection system 1 includes a laser beam source (a light generating unit) 2. The laser beam source 2 is operated by a first power source 3, and emits light to be irradiated the semiconductor device 10. The light emitted from the laser beam source 2 is optically guided to a scan optical system 7 via a polarization preservation single mode optical fiber 5 for probe light. The scan optical system 7 has a scan head 8 and a lens system 9. Accordingly, the light optically guided to the scan optical system 7 is imaged on a predetermined position of the semiconductor device 10, and an irradiation zone of the light is two-dimensionally scanned with respect to the semiconductor device 10. Further, the scan optical system 7 and the semiconductor device 10 are disposed in a black box 6.

The light reflected by the semiconductor device 10 when the light emitted from the laser beam source 2 is irradiated the semiconductor device 10 is optically guided to an optical sensor (a light detecting unit) 12 via an optical fiber 11 for optical feedback. The optical sensor 12 is operated by a second power source 13 installed separately from the first power source 3, and detects the reflected light to output a detection signal. The detection signal output from the optical sensor 12 is input into a spectrum analyzer (a signal generating unit) 15 via an amplifier 14. A spectrum analyzer 15 is electrically coupled to a control device 18 via a frequency band setting unit 16 and a signal acquisition unit 17. The control device 18 forms a semiconductor device image based on an analysis signal acquired by the signal acquisition unit 17, and displays the semiconductor device image on a display device 19.

A laser scan controller 21 is electrically coupled to the control device 18. The laser scan controller 21 controls the laser beam source 2 and the scan optical system 7. A tester unit (an electrical signal application unit) 22 including a tester, a pulse generator and a power source is electrically coupled to the spectrum analyzer 15. The tester unit 22 applies an electrical signal having a predetermined modulation frequency to the semiconductor device 10. Accordingly, the semiconductor device 10 is driven upon inspection.

Figure 2:
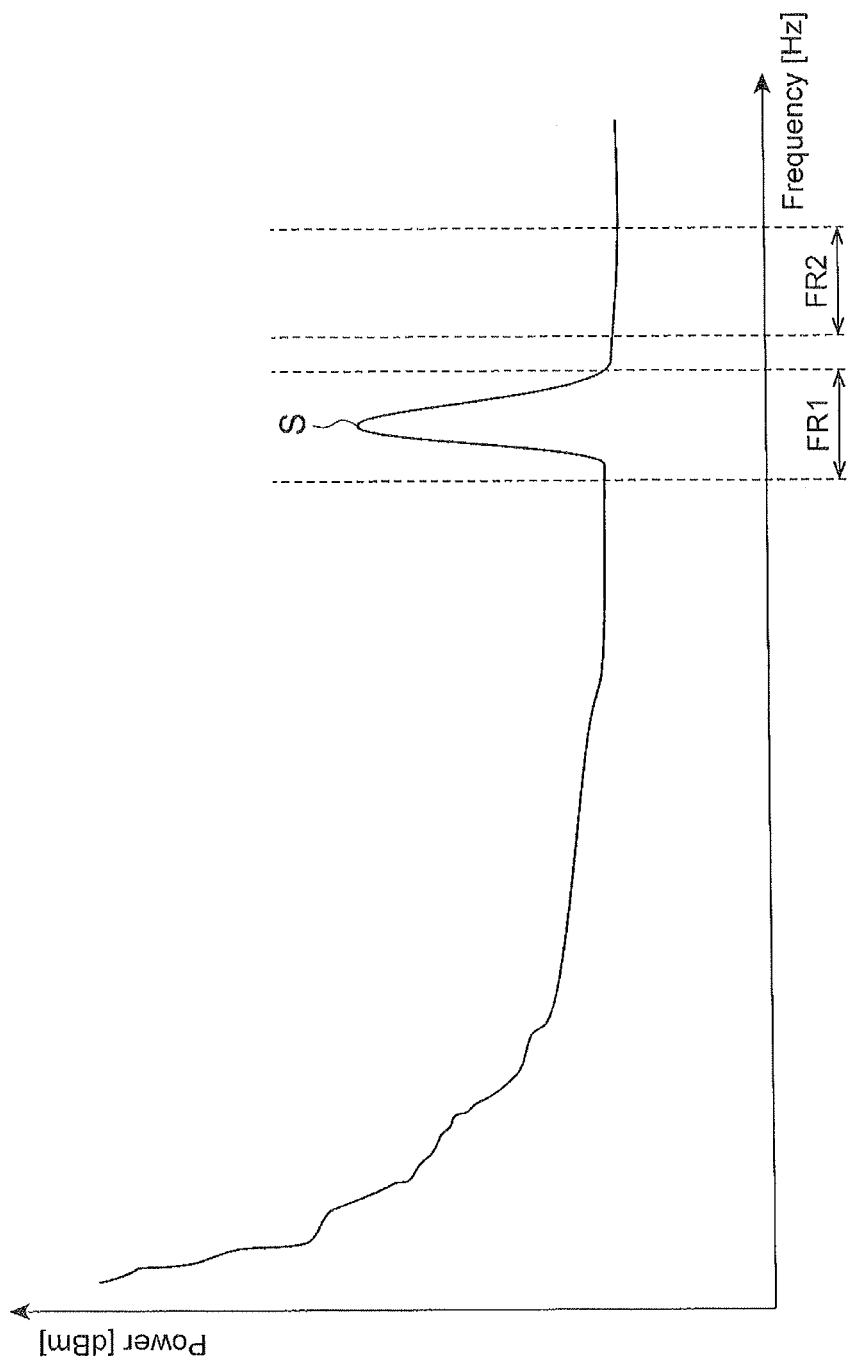
FIG. 2 is a graph showing a frequency property of a detection signal for describing a first setting example of a measurement frequency band and a reference frequency band in the semiconductor device inspection system of FIG. 1.

Next, the frequency band setting unit 16, the spectrum analyzer 15 and the signal acquisition unit 17 will be described in detail. As shown in FIG. 2, the frequency band setting unit 16 sets a measurement frequency band FR1 and a reference frequency band FR2 with respect to the detection signal input into the spectrum analyzer 15. The measurement frequency band FR1 is a frequency band including a frequency of a measurement signal S (a frequency N times (N is a natural number) a modulation frequency of an electrical signal applied to the semiconductor device 10). Meanwhile, the reference frequency band FR2 is a frequency band set to remove the noise from the detection signal in the measurement frequency band FR1.

Figure 3:
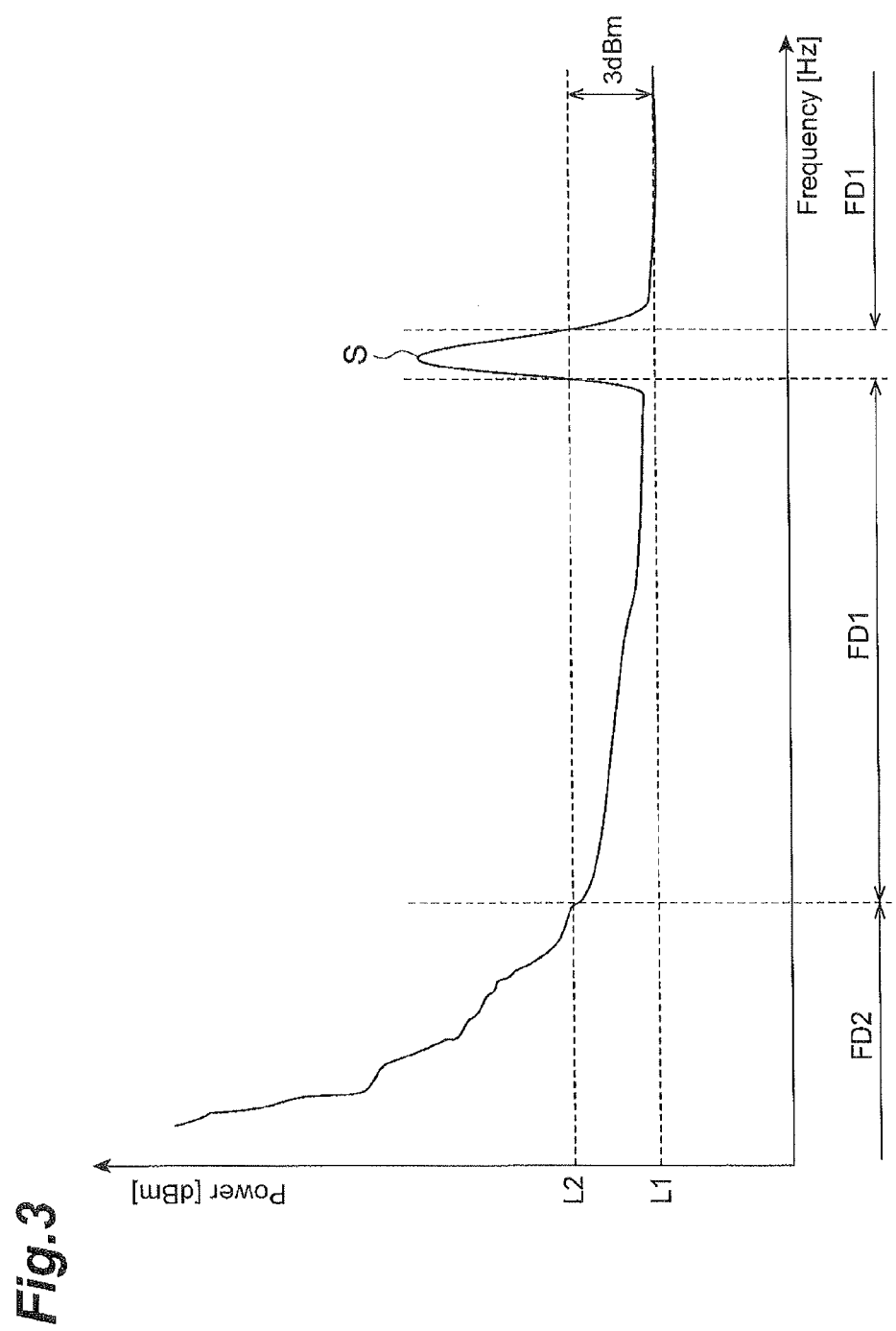
FIG. 3 is a graph showing a frequency property of a detection signal for describing a frequency domain in which a reference frequency band can be set in the semiconductor device inspection system of FIG. 1.

As shown in FIG. 3, when the level of the detection signal is calculated based on the power, the frequency band setting unit 16 sets the reference frequency band FR2 to a frequency domain. FD1 in which the level is lower than a level L2 obtained by adding 3 decibels to a white noise level L1 serving as a reference. This means that the level L2 is about two times the white noise level L1 ($10 \log_{10} L2 - 10 \log_{10} L1 = 10 \log_{10}(L2/L1) = 3$, $L2 \approx L1 \times 2$). Further, when the level of the detection signal is calculated based on amplitude energy, the reference frequency band FR2 is set to the frequency domain FD1 lower than the level L2 obtained by adding 6 decibels to the white noise level L1 serving as the reference ($20 \log_{10} L2 - 20 \log_{10} L1 = 20 \log_{10}(L2/L1) = 6$, $L2 \approx L1 \times 2$).

As an example, the white noise level L1 serving as the reference is a white noise level generated in the measurement frequency band FR1 when light is irradiated a predetermined zone (a measurement zone or a reference zone) of the semiconductor device 10 and the light reflected by the predetermined zone is detected, in a state in which the semiconductor device 10 is not driven (i.e., in a state in which an electrical signal is not input from the tester unit 22). Further, the frequency band setting unit 16 can previously set a zone in which the reference frequency band FR2 is set, with no need to detect the white noise level L1 serving as the reference and the frequency domain FD1 for setting the reference frequency band FR2 with each measurement. In a first example shown in FIG. 2, the frequency band setting unit 16 sets the reference frequency band FR2 to the frequency domain FD1 having a frequency higher than the measurement frequency band FR1. This is because, as shown in FIG. 3, there is a tendency for a frequency domain FD2 in which 1/F noise appears to be in a frequency domain having a frequency lower than the measurement frequency band FR1.

The spectrum analyzer 15 generates a measurement signal from the detection signal in the measurement frequency band FR1, and generates a reference signal from the detection signal in the reference frequency band FR2. In this way, the spectrum analyzer 15 can simultaneously perform generation of signals in the plurality of frequency bands. For example, a cross domain analyzer from Advantest Corp. is provided as such a spectrum analyzer. The signal acquisition unit 17 acquires an analysis signal as a difference between the generated measurement signal and the reference signal is calculated by the spectrum analyzer 15. Accordingly, the analysis signal from which the shot noise, the excess noise, and so on, are removed can be acquired.

Figure 4:
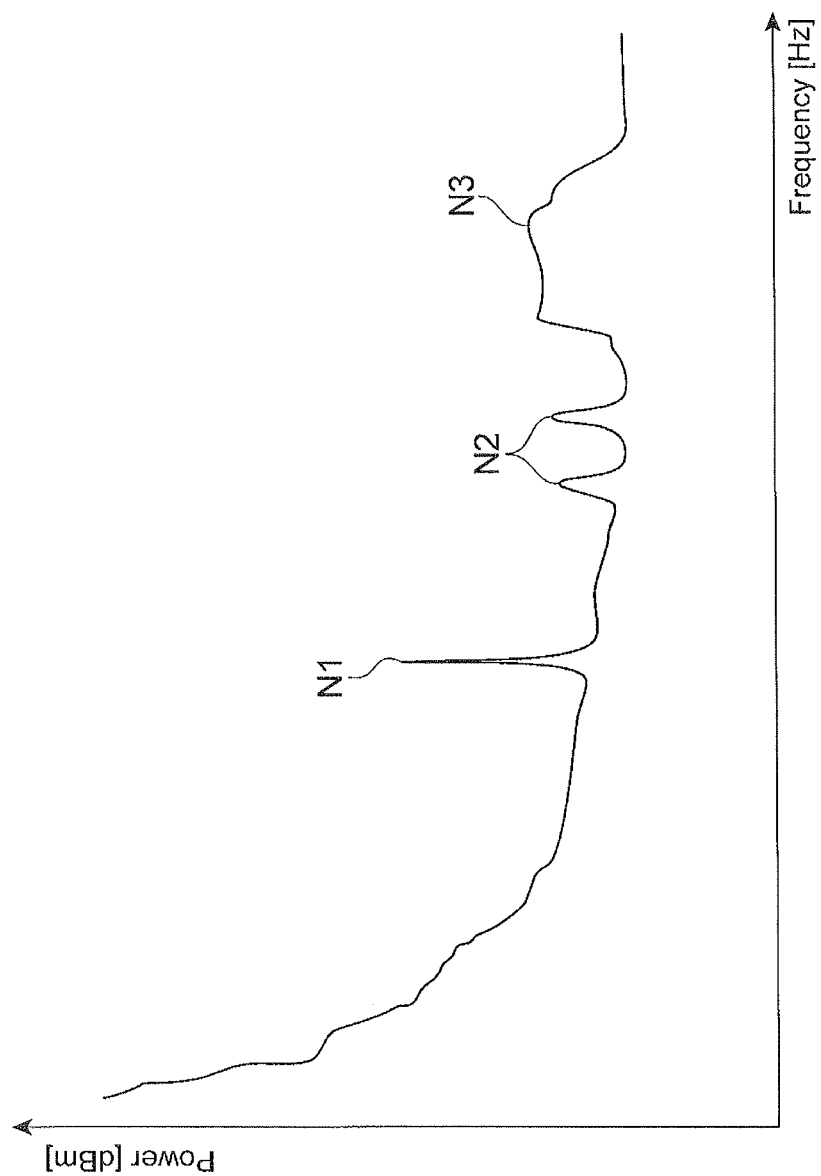
FIG. 4 is a graph showing a frequency property of a detection signal when a system noise overlaps a white noise.

Next, removal of the noise in the signal acquisition unit 17 will be described in detail. In the optical probing technology, as shown in FIG. 4, S/N is defined by a system noise such as a system noise N1 related to the optical sensor 12, a system noise N2 related to the laser beam source 2, a system noise N3 related to a circuit operation, and so on, in addition to the white noise such as the shot noise of the reflected light, the excess noise of the laser beam source 2, the thermal noise of the optical sensor 12, and so on.

The shot noise is shown as a current noise $i_{sn}$, and is represented as the following equation when an electric charge of electrons is e, a light current is $I_D$, a dark current is $I_d$, and an observed frequency band is $\Delta f$. On the other hand, the excess noise is in proportion to a quantity of the light, and a multiplier thereof is varied according to the laser beam source 2.

$$\overline{i_{sn}^2} = 2e(I_D + I_d)\Delta f \quad \text{[Math. 1]}$$

In the optical probing technology, the shot noise and the excess noise are increased depending upon the quantity of the reflected light. Specifically, the shot noise is in proportion to a square root of the quantity of light, and the excess noise is in proportion to the quantity of light. As a result, when mapping is performed in a state in which the noise components overlap, as shown in FIGS. 5(a) and 5(b), an image (a semiconductor device image of FIG. 5(a), corresponding to a semiconductor device image based on the above-mentioned measurement signal) similar to a pattern image noise (a semiconductor device image of FIG. 5(b), corresponding to a semiconductor device image based on the above-mentioned reference signal) is obtained.

Here, the shot noise cannot be fundamentally removed, and the shot noise component cannot be prevented from overlapping the measurement result as the pattern image. Moreover, the excess noise component in proportion to the quantity of light also overlaps the measurement result, in addition to the shot noise component in proportion to the square root of the quantity of light. Accordingly, it is difficult to remove the shot noise and the excess noise in the image processing of the simple pattern image.

Here, in the optical probing technology of the related art, in the detection signal of the reflected light, a signal of a predetermined frequency band is detected. As the amplitude image, the phase image and the IQ image obtained at this time are displayed on the display device, an operation state of the semiconductor device can be detected. However, as described above, the image noise depending on strength of the reflected light from a surface of the semiconductor device overlaps the signal of the amplitude image, like the pattern image. For this reason, even when the signals are added to improve the S/N of the image, the image noise covers the signal without disappearing. Further, the generally used lock-in method (an S/N improvement technique by acquisition of a frequency synchronized with respect to a pulse stream of a signal) is the same as this method so far.

According to the above-mentioned semiconductor device inspection system 1, the above-mentioned problems can be solved. First, it is necessary to remove the system noise (see FIG. 4) such as the system noise N1 related to the optical sensor 12, the system noise N2 related to the laser beam source 2, the system noise N3 related to the circuit operation, and so on. For this reason, as the first power source 3 for the laser beam source 2 and the second power source 13 for the optical sensor 12 are separately installed, the system noises N1 and N2 caused by a digital power source such as a switching power source, a DD converter, and so on, are removed. In addition, as the laser beam source 2, the optical sensor 12, and so on, are controlled from the outside without using the IC used to control the laser beam source 2, the optical sensor 12, and so on, the system noise N3 related to the circuit operation is removed.

Then, upon the measurement, a range in which the measurement signal S is present is selected as a center frequency, and a bandwidth of the measurement frequency band FR1 is set directly or as a time constant. In addition, at a frequency domain that deviates slightly from the center frequencies (for example, at a frequency domain that is continuously adjoined), the bandwidth of the reference frequency band FR2 is set directly or as a time constant to have the same bandwidth as the measurement frequency band FR1. When there is no noise particularly depending on the frequency, a noise level when measured at the same bandwidth or time constant becomes equal at near frequencies.

Next, the power in the frequency of the measurement frequency band FR1 is converted into the amplitude energy. In addition, the power in the frequency of the reference frequency band FR2 is also converted into the amplitude energy. Then, when a difference between the converted amplitude energy is taken, the amplitude energy from which the shot noise, the excess noise, and so on, are removed can be acquired. As the mapping is performed based on the amplitude energy, as shown in FIG. 5(c), an optical signal map (corresponding to the semiconductor device image based on the above-mentioned analysis signal) modulated by a response of the semiconductor device 10 can be obtained in real time.

As described above, in the semiconductor device inspection system 1, a semiconductor device inspection method including a light detection step of irradiating the semiconductor device 10 with light, detecting the light reflected by the semiconductor device 10 and outputting a detection signal, a frequency band setting step of setting the measurement frequency band FR1 and the reference frequency band FR2 with respect to the detection signal, a signal generating step of generating a measurement signal from the detection signal in the measurement frequency band FR1 and generating a reference signal from the detection signal in the reference frequency band FR2, and a signal acquisition step of acquiring an analysis signal by calculating a difference between the measurement signal and the reference signal is performed. Then, in the frequency band setting step, when the level of the detection signal is calculated based on the power, the reference frequency band FR2 is set to the frequency domain FD1 in which the level is lower than the level L2 obtained by adding 3 decibels to the white noise level L1 serving as the reference. In other words, in the frequency band setting step, when the level of the detection signal is calculated based on the amplitude energy, the reference frequency band FR2 is set to the frequency domain FD1 in which the level is lower than the level L2 obtained by adding 6 decibels to the white noise level L1 serving as the reference.

In this way, in the semiconductor device inspection system 1, the measurement signal and the reference signal are generated based on the detection signal in the measurement frequency band FR1 and the detection signal in the reference frequency band FR2 detected at the same timing. Here, when the level of the detection signal is calculated based on the power, the reference frequency band FR2 is set to the frequency domain FD1 in which the level is lower than the level L2 obtained by adding 3 decibels to the white noise level L1 serving as the reference. Accordingly, the analysis signal acquired by calculating the difference between the measurement signal and the reference signal is in a state in which the shot noise, the excess noise, and so on, are removed. In this way, since the detection signal in the measurement frequency band FR1 and the detection signal in the reference frequency band FR2 are detected at the same timing, in comparison with the case in which these are detected at separate timings, the measurement time can be reduced. Moreover, since the detection signal in the measurement frequency band FR1 and the detection signal in the reference frequency band FR2 are detected under the same condition, the measurement result can be obtained with higher precision than when these are detected under different conditions.

Further, as a cumulative time (a cumulative number) of a band filter or a detection signal is adjusted, sufficient signal strength in which the measurement signal exceeds the level L2 can be secured. However, if the reference frequency band FR2 is set to the frequency domain exceeding the level L2, when the difference between the measurement signal and the reference signal is taken, not only the noise component but also the signal component disappears.

In addition, in the semiconductor device inspection system 1, the frequency band setting unit 16 sets the reference frequency band FR2 to the frequency domain FD1 in which the frequency is higher than the measurement frequency band FR1. Accordingly, an influence of the 1/F noise having a tendency to appear in a relatively low frequency domain can be suppressed from being applied to the detection signal in the measurement frequency band FR1.

In addition, in the semiconductor device inspection system 1, the first power source 3 for the laser beam source 2 and the second power source 13 for the optical sensor 12 are separately installed. Accordingly, since there is no need to install the DD converter or the like that causes the system noise, occurrence of the system noise in the frequency domain FD1 in which the reference frequency band FR2 is set can be suppressed. In order to acquire the analysis signal from which the shot noise, the excess noise, and so on, are removed by calculating the difference between the measurement signal and the reference signal, since occurrence of the system noise in the frequency domain FD1 in which the reference frequency band FR2 is set needs to be suppressed, the configuration is extremely important.

In addition, in the semiconductor device inspection system 1, the spectrum analyzer 15 capable of simultaneously performing generation of the signals in the plurality of frequency bands is used. Accordingly, the measurement signal and the reference signal can be efficiently generated based on the detection signal in the measurement frequency band FR1 and the detection signal in the reference frequency band FR2 detected at the same timing.

Further, the setting of the measurement frequency band FR1 and the reference frequency band FR2 can be performed as will be described below. For example, a frequency property of the detection signal is displayed on the display device 19, and a user can manually set the frequency bands FR1 and FR2 while checking the screen. In addition, a peak frequency of the power can be set, the measurement frequency band FR1 can be automatically set based on the peak frequency, and the reference frequency band FR2 can be automatically set within a range deviated to an extent of the set frequency. In addition, the modulation frequency of the electrical signal applied to the semiconductor device 10 is acquired, and the measurement frequency band FR1 can be automatically set include the frequency N times (N is a natural number) the modulation frequency. In this case, the setting of the measurement frequency band FR1 can be optimally performed.

In addition, as the light regularly reflected by the reference sample (a mirror or the like) is measured, the frequency-dependent noise generated by the laser beam source 2 can acquire the generated frequency. In addition, when measured without the light entering, the frequency-dependent noise generated by another device can be acquired, and thus the generated frequency can be acquired.

In addition, calculation of the difference between the measurement signal and the reference signal may be performed in each pixel, or may be performed in the entire screen. In addition, when two frequencies are simultaneously observed, as the measurement frequency band FR1 and the reference frequency band FR2 are set to the two frequencies and calculation of the difference between the measurement signal and the reference signal is performed with respect to these, one signal with respect to an average can be displayed as a positive value and the other signal can be displayed as a negative value while removing the shot noise, the excess noise, and so on.

Figure 6:
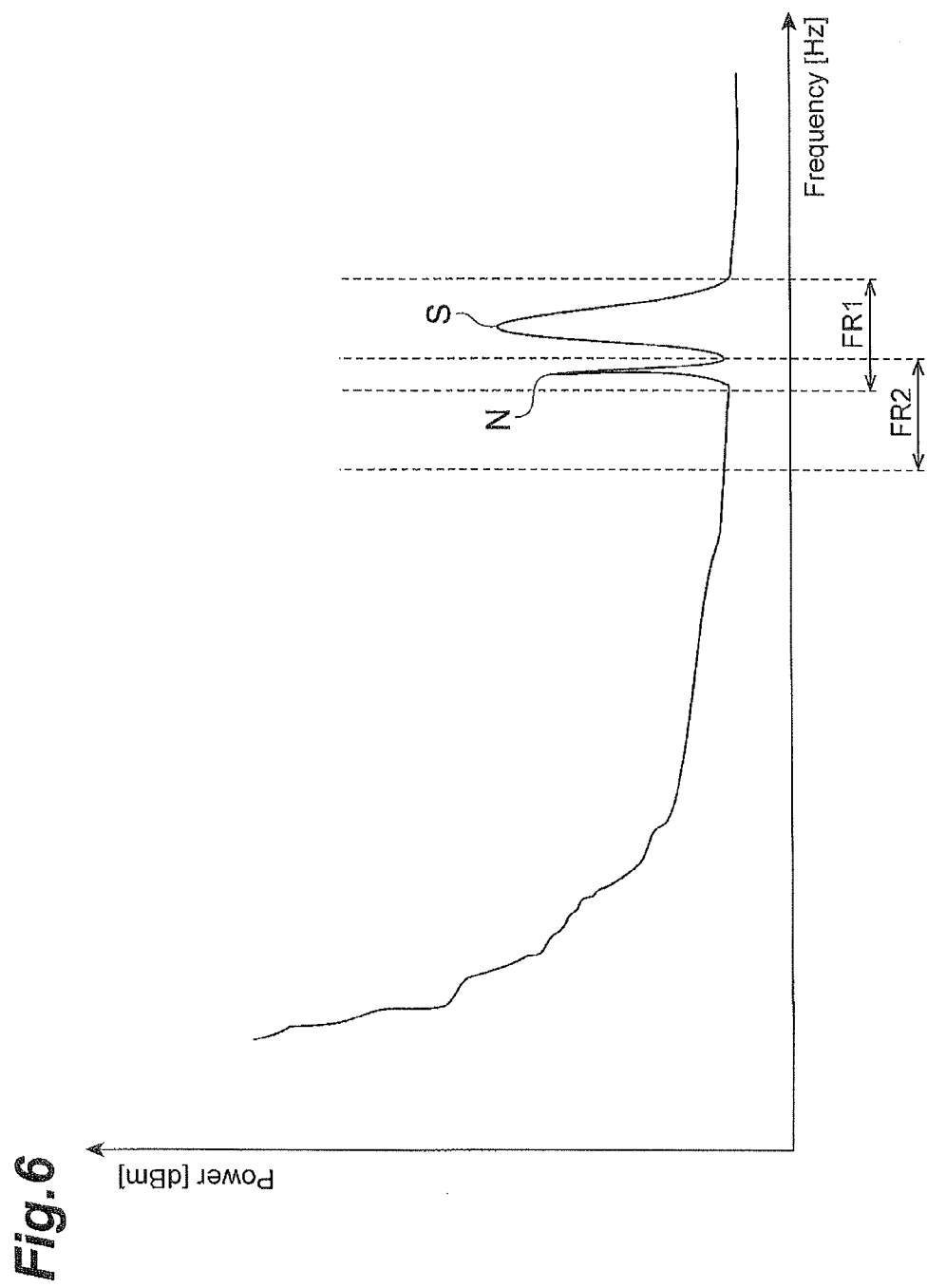
FIG. 6 is a graph showing a frequency property of a detection signal for describing a second setting example of the measurement frequency band and the reference frequency band in the semiconductor device inspection system of FIG. 1.

FIG. 6 is a graph showing a frequency property of a detection signal for describing a second setting example of the measurement frequency band FR1 and the reference frequency band FR2. As shown in FIG. 6, for example, when a system noise N that cannot be eliminated is present in the vicinity of the measurement signal S, the frequency band setting unit 16 sets the reference frequency band FR2 to include the frequency of the system noise N included in the measurement frequency band FR1. That is, the measurement frequency band FR1 and the reference frequency band FR2 are set such that both include the system noise N. Accordingly, as the difference between the measurement signal and the reference signal are calculated, the system noise N can be removed from the analysis signal. In particular, the technique is effective in a sample in which the reference signal cannot be obtained, a base clock is unstable, and RBW should be widened. Further, for example, when the frequency of the measurement signal S can be shifted with respect to the frequency of the system noise N that cannot be eliminated, the measurement frequency band FR1 and the reference frequency band FR2 may be set not to include the frequency of the system noise N.

Figure 7:
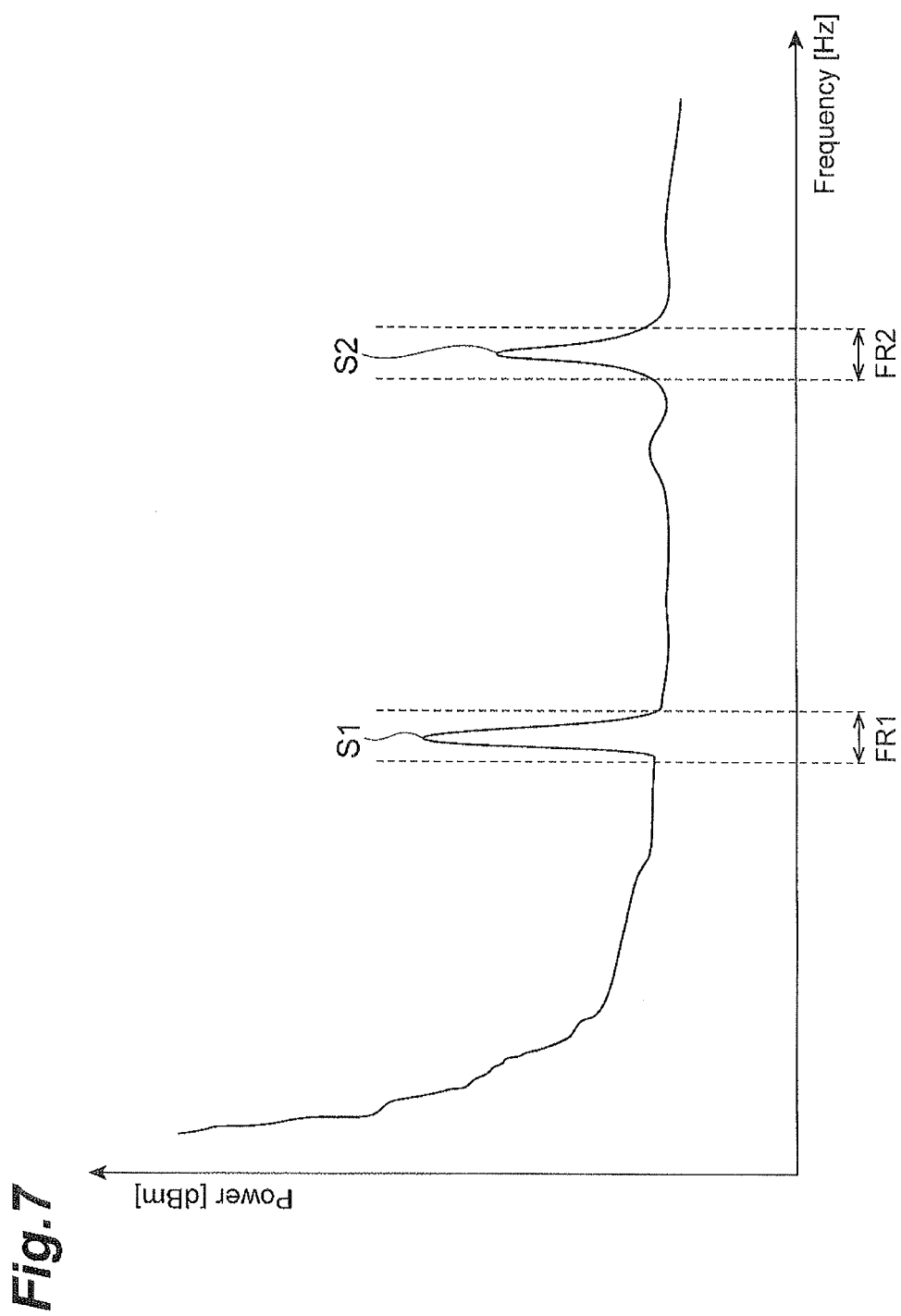
FIG. 7 is a graph showing a frequency property of a detection signal for describing a third setting example of the measurement frequency band and the reference frequency band in the semiconductor device inspection system of FIG. 1.
Figure 8:
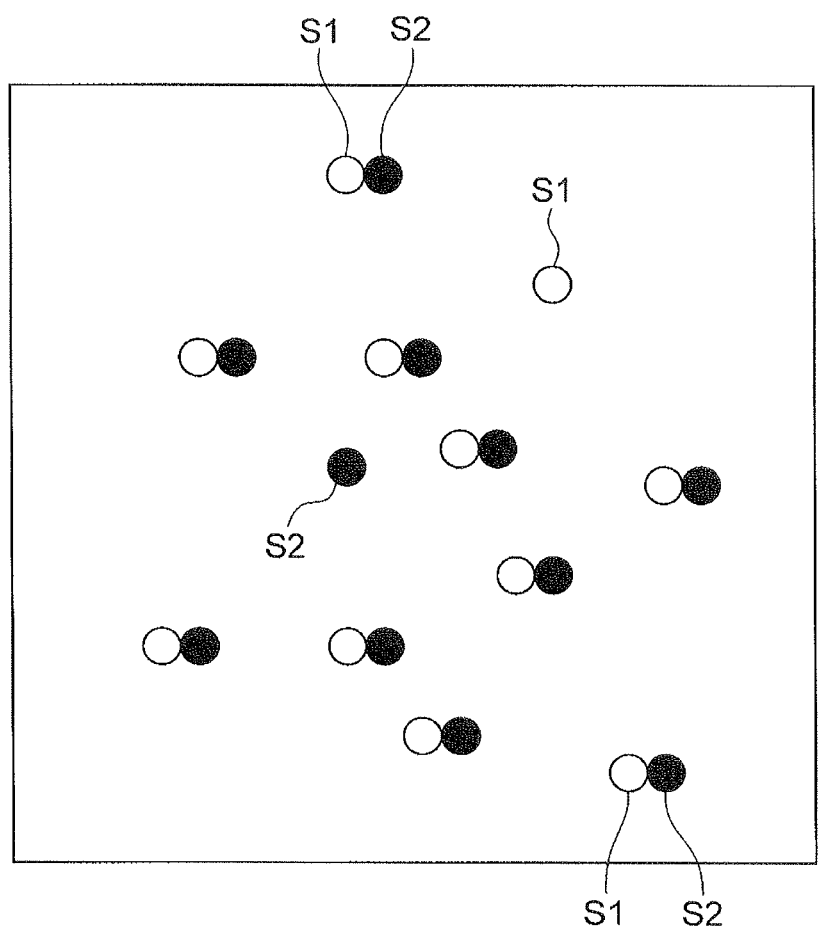
FIG. 8 shows a semiconductor device image based on an analysis signal acquired by the semiconductor device inspection system of FIG. 1 in the case of FIG. 7.

FIG. 7 is a graph showing a frequency property of a detection signal for describing a third setting example of the measurement frequency band FR1 and the reference frequency band FR2. As shown in FIG. 7, for example, when the tester unit 22 applies a first electrical signal E1 having a first modulation frequency and a second electrical signal E2 having a second modulation frequency different from the first modulation frequency (for example, a flip flop and clock buffer for data) to the semiconductor device 10 and the modulations by these signals are simultaneously observed, the frequency band setting unit 16 sets the measurement frequency band FR1 and the reference frequency band FR2 based on the first modulation frequency of the first electrical signal E1 and the second modulation frequency of the second electrical signal E2. That is, the measurement frequency band FR1 is set to include a frequency N times (N is a natural number) the first modulation frequency of the first electrical signal E1, and the reference frequency band FR2 is set to include a frequency N times (N is a natural number) the second modulation frequency of the second electrical signal E2. Accordingly, as the difference between the measurement signal S1 based on the measurement frequency band FR1 and the measurement signal S2 based on the reference frequency band FR2 are calculated, in addition to the measurement frequency band FR1, even in the reference frequency band FR2, a separate analysis signal from which the shot noise, the excess noise, and so on, are removed can be acquired. Then, as shown in FIG. 8, the semiconductor device image separated by color in which a zone corresponding to the measurement signal S1 is white and a zone corresponding to the measurement signal S2 is black can be obtained.

Figure 9:
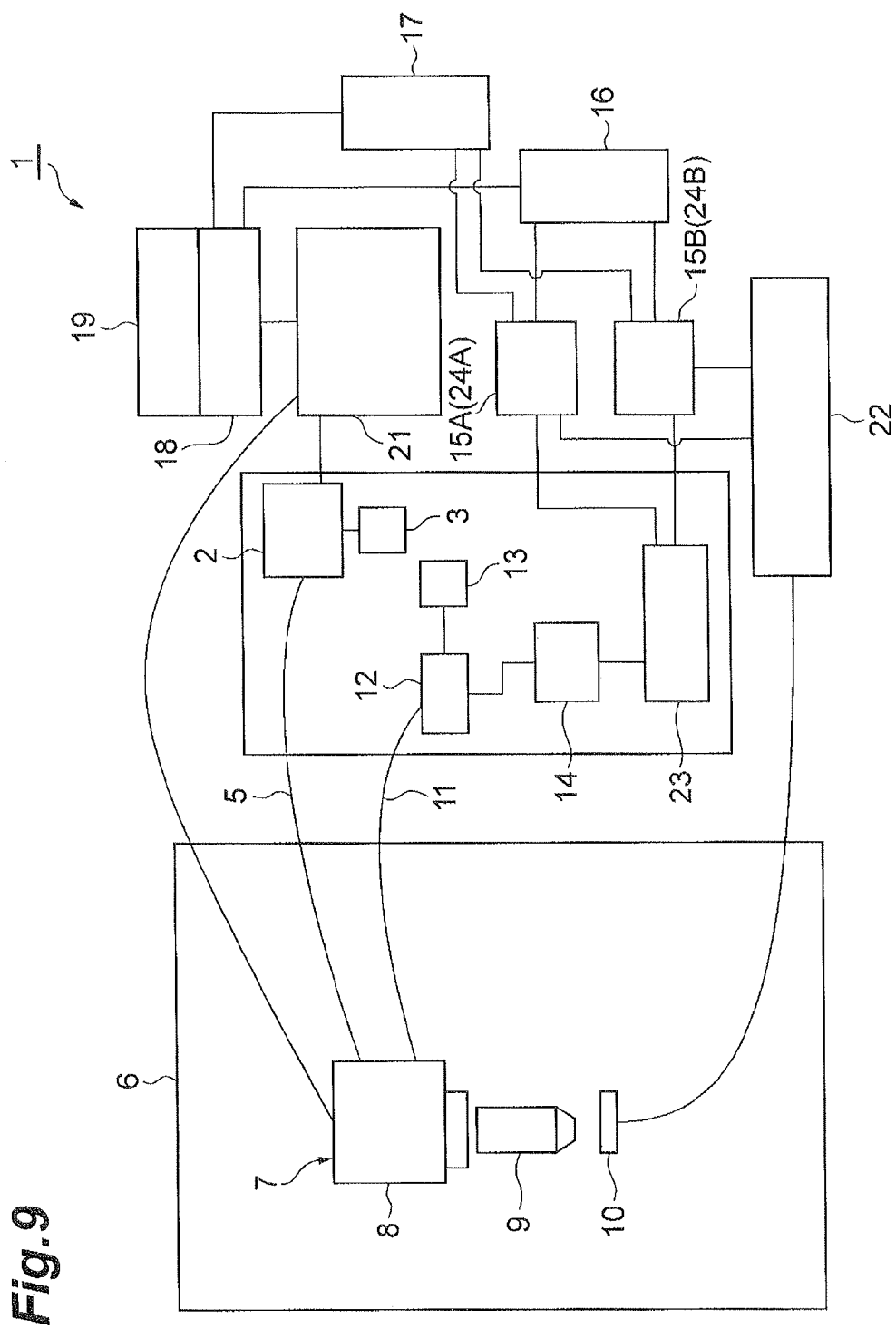
FIG. 9 is a configuration view of a semiconductor device inspection system of another embodiment of the present invention.

Hereinabove, while embodiments of the present invention have been described, the present invention is not limited to the embodiments. For example, the light generating unit that generates light to be irradiated the semiconductor device is not limited to the laser beam source 2 but may be another light source such as a super luminescent diode or the like. In addition, instead of the electrical signal, heat may be applied to the semiconductor device 10. In this case, the measurement frequency band FR1 is set to include the frequency N times (N is a natural number) the modulation frequency of the heat applied to the semiconductor device 10. In addition, as shown in FIG. 9, the semiconductor device inspection system 1 may include, instead of the spectrum analyzer 15 that can simultaneously perform generation of the signals of the plurality of frequency bands, a first spectrum analyzer (a signal generating unit) 15A that generates a measurement signal from the detection signal in the measurement frequency band FR1, and a second spectrum analyzer (a signal generating unit) 15B that generates a reference signal from the detection signal in the reference frequency band FR2. In this case, the detection signal output from the amplifier 14 is branched off by a branch circuit 23, and input into the spectrum analyzers 15A and 15B. Further, the semiconductor device inspection system 1 may include, instead of the spectrum analyzers 15A and 15B, a first lock-in amplifier (a signal generating unit) 24A that generates a measurement signal from the detection signal in the measurement frequency band FR1, and a second lock-in amplifier (a signal generating unit) 24B that generates a reference signal from the detection signal in the reference frequency band FR2. In all of the configurations the measurement signal and the reference signal can be efficiently generated based on the detection signal in the measurement frequency band FR1 and the detection signal in the reference frequency band FR2, which are detected at the same timing. In addition, the reference frequency band FR2 may be set to a frequency domain higher than a maximum frequency of the frequency domain FD2 in which 1/F noise appears and lower than a frequency N times (N is a natural number) the modulation frequency of the electrical signal applied to the semiconductor device 10.

REFERENCE SIGNS LIST

1 . . . semiconductor device inspection system, 2 . . . laser beam source (light generating unit), 3 . . . first power source, 10 . . . semiconductor device, 12 . . . optical sensor (light detecting unit), 13 . . . second power source, 15 . . . spectrum analyzer (signal generating unit), 15A . . . first spectrum analyzer (signal generating unit), 15B . . . second spectrum analyzer (signal generating unit), 16 . . . frequency band setting unit, 17 . . . signal acquisition unit, 22 . . . tester unit (electrical signal application unit), 24A . . . first lock-in amplifier (signal generating unit), 24B . . . second lock-in amplifier (signal generating unit)

The invention claimed is:

1. A system for inspecting a semiconductor device serving as a device under test, the system comprising:
    a light source configured to generate light to be irradiated the semiconductor device;
    a light detector configured to detect reflected light that is reflected from the semiconductor device and output a detection signal;
    a frequency band setting unit configured to set a measurement frequency band and a reference frequency band with respect to the detection signal;
    a signal generating unit electrically coupling the frequency band setting unit and configured to generate a measurement signal from the detection signal in the measurement frequency band and generate a reference signal from the detection signal in the reference frequency band; and
    a signal acquisition unit electrically coupling the signal generating unit and configured to calculate a difference between the measurement signal and the reference signal to acquire an analysis signal,
    wherein, when a level of the detection signal is calculated based on power, the frequency band setting unit sets the reference frequency band to a frequency domain in which the level is lower than a level obtained by adding 3 decibels to a white noise level serving as a reference.

2. The system according to claim 1, wherein the frequency band setting unit sets the reference frequency band to the frequency domain having a frequency higher than the measurement frequency band.

3. The system according to claim 1, wherein the frequency band setting unit sets the reference frequency band to include a frequency of a system noise included in the measurement frequency band.

4. The system according to claim 1, further comprising an electrical signal application unit configured to apply a first electrical signal having a first modulation frequency to the semiconductor device,
    wherein the frequency band setting unit sets the measurement frequency band to include a frequency that is a natural number times the first modulation frequency.

5. The system according to claim 4, wherein the electrical signal application unit applies a second electrical signal having a second modulation frequency different from the first modulation frequency to the semiconductor device together with the first electrical signal, and
    the frequency band setting unit sets the measurement frequency band to include a frequency that is a natural number times the first modulation frequency, and sets the reference frequency band to include a frequency that is a natural number times the second modulation frequency.

6. The system according to claim 1, further comprising:
a first power source configured to operate the light source; and
a second power source separately installed from the first power source and configured to operate the light detector.

7. The system according to claim 1, wherein the signal generating unit comprises a spectrum analyzer configured to generate the measurement signal from the detection signal in the measurement frequency band and generate the reference signal from the detection signal in the reference frequency band.

8. The system according to claim 1, wherein the signal generating unit comprises a first lock-in amplifier configured to generate the measurement signal from the detection signal in the measurement frequency band, and a second lock-in amplifier configured to generate the reference signal from the detection signal in the reference frequency band.

9. The system according to claim 1, wherein the signal generating unit comprises a first spectrum analyzer configured to generate the measurement signal from the detection signal in the measurement frequency band, and a second spectrum analyzer configured to generate the reference signal from the detection signal in the reference frequency band.

10. A system for inspecting a semiconductor device inspection serving as a device under test, the system comprising:
a light source configured to generate light to be irradiated the semiconductor device;
a light detector configured to detect reflected light that is reflected from the semiconductor device and output a detection signal;
a frequency band setting unit configured to set a measurement frequency band and a reference frequency band with respect to the detection signal;
a signal generating unit electrically coupling the frequency band setting unit and configured to generate a measurement signal from the detection signal in the measurement frequency band and generate a reference signal from the detection signal in the reference frequency band; and
a signal acquisition unit electrically coupling the signal generating unit and configured to calculate a difference between the measurement signal and the reference signal to acquire an analysis signal,
wherein, when a level of the detection signal is calculated based on amplitude energy, the frequency band setting unit sets the reference frequency band to a frequency domain in which the level is lower than a level obtained by adding 6 decibels to a white noise level serving as a reference.

11. A method for inspecting a semiconductor device serving as a device under test, the method comprising:
irradiating the with light;
detecting reflected light that is reflected from the semiconductor device and outputting a detection signal;
setting a measurement frequency band and a reference frequency band with respect to the detection signal;
generating a measurement signal from the detection signal in the measurement frequency band and generating a reference signal from the detection signal in the reference frequency band; and
calculating a difference between the measurement signal and the reference signal to acquire an analysis signal,
wherein, in the setting, when a level of the detection signal is calculated based on power, the reference frequency band is set to a frequency domain in which the level is lower than a level obtained by adding 3 decibels to a white noise level serving as a reference.

12. A method for inspecting a semiconductor device serving as a device under test, the method comprising:
irradiating the semiconductor device with light,
detecting reflected light that is reflected from the semiconductor device and outputting a detection signal;
setting a measurement frequency band and a reference frequency band with respect to the detection signal;
generating a measurement signal from the detection signal in the measurement frequency band and generating a reference signal from the detection signal in the reference frequency band; and
calculating a difference between the measurement signal and the reference signal to acquire an analysis signal,
wherein, in the setting, when a level of the detection signal is calculated based on amplitude energy, the reference frequency band is set to a frequency domain in which the level is lower than a level obtained by adding 6 decibels to a white noise level serving as a reference.

* * * * *